US00PP32762P2

(12) United States Plant Patent
Stemkens

(10) Patent No.: US PP32,762 P2
(45) Date of Patent: Jan. 19, 2021

(54) ***LEUCANTHEMUM* PLANT NAMED 'LEUZ0006'**

(50) Latin Name: *Leucanthemum maximum*
Varietal Denomination: LEUZ0006

(71) Applicant: SYNGENTA CROP PROTECTION AG, Basel (CH)

(72) Inventor: Henricus Godefridus Wilhelmus Stemkens, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/602,583

(22) Filed: Nov. 5, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285, 263.1, 284
CPC ..... A01H 5/02; A01H 5/00; A01H 6/14
See application file for complete search history.

(56) References Cited

PUBLICATIONS

Syngenta Flowers 2019/2020 Cuttings Collection, retrieved on Aug. 12, 2020, retrieved from the Internet at http://www.gradinaspa.com/part/19%20Katalog%20SYNGENTA%20FLOWERS%20Cuttings%202019-2020.pdf, pp. 9, 67, 81, 106, 108. (Year: 2020).*

* cited by examiner

*Primary Examiner* — June Hwu
(74) *Attorney, Agent, or Firm* — Dale Skalla

(57) ABSTRACT

A new *Leucanthemum* plant named 'LEUZ0006' characterised particularly by the fact that it does not need cold to flower, has abundant flowers on a compact plant and has quite small flowers with a creamy yellow color.

1 Drawing Sheet

Latin name of the genus and species of the plant claimed: *Leucanthemum maximum.*

Varietal denomination: 'LEUZ0006'.

BACKGROUND OF THE NEW PLANT

The present invention comprises a new distinct cultivar of *Leucanthemum*, botanically known as *Leucanthemum maximum.*

The new *Leucanthemum* is a product of a planned breeding program conducted in Enkhuizen, The Netherlands. The objective of the breeding program was to develop a new *Leucanthemum* cultivar with a cream-yellow flower that is floriferous, single-flowering, good flower quality and a good vigor that does not require cold to flower.

The present cultivar originated from an open pollinated cross made in 2011 of a *Leucanthemum* selection identified as 'S4463-2', not patented, as the female, or seed parent, with a cloud of pollen of the whole *Leucanthemum* population.

The present cultivar has been repeatedly asexually reproduced by terminal cuttings in Enkhuizen, Netherlands.

The distinctive characters of this new *Leucanthemum* are stable and reproduced true to type in successive generations of asexual reproduction. It takes 9 to 13 weeks to produce a finished plant, depending on the temperature and day length.

This new *Leucanthemum* plant is a perennial in zones 4-9 in the US.

BRIEF SUMMARY OF INVENTION

'LEUZ0006' has not been observed under all possible environmental conditions. The phenotype may vary significantly with variations in environment such as temperature, light intensity and day length.

A Plant Breeder's Right for this cultivar has not yet been applied for. 'LEUZ0006' has not been made publicly available prior to the effective filing date of this application, notwithstanding any disclosure that may have been made less than one year prior to the effective filing date of this application by the inventor or another who obtained 'LEUZ0006' directly from the inventor.

The following traits have been repeatedly observed and are determined to be basic characteristics of the new variety. The combination of these characteristics distinguishes this *Leucanthemum* as a new and distinct variety.

BRIEF DESCRIPTION OF THE PHOTOGRAPHS

The accompanying photographic drawings show typical flower and foliage characteristics of 'LEUZ0006' with colors being as true as possible with an illustration of this type.

Figure 1:
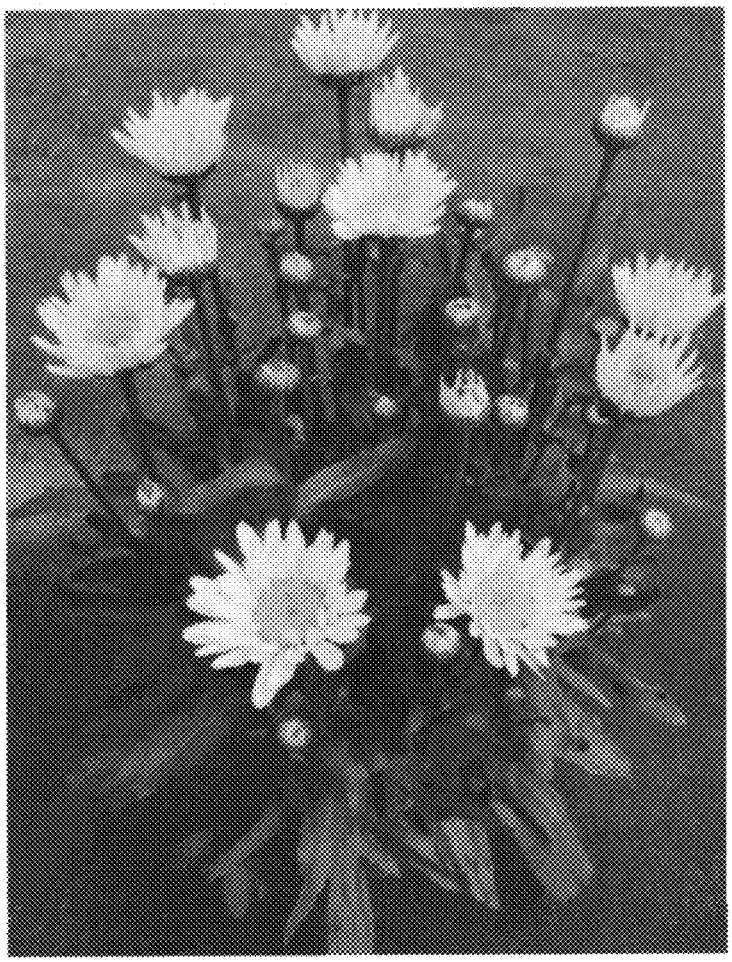
Figure 2:
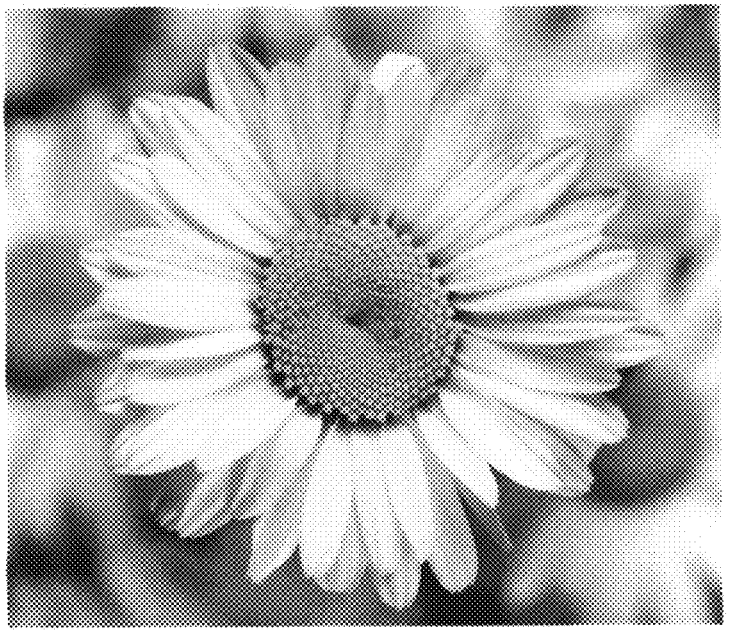

The photographic drawings show in FIG. 1 blooms, buds and foliage of the plant in full color and in FIG. 2 a close-up of the flower.

DETAILED BOTANICAL DESCRIPTION

The following detailed descriptions set forth the distinctive characteristics of this new *Leucanthemum*. The data which defines these characteristics were collected from asexual reproductions carried out in Enkhuizen, Netherlands. The plant description was taken on 14 weeks old plants, blossomed under natural light on the container field.

Color references are made to The Royal Horticultural Society Colour Chart (R.H.S.) 2001.

Plants of the new *Leucanthemum* and the female parent differ in: 1) The female has bigger flowers than 'LEUZ0006' 2) The female has a lighter flower color than 'LEUZ0006' and 3) The female has longer flower stems than 'LEUZ0006'.

Natural flowering season at specified location(s): Under Northern European conditions, 'LEUZ0006' flowers from June till the end of September.

The following traits distinguish 'LEUZ0006' as a new and distinct cultivar:

The plant does not require cold to flower

The flowers are single

The flowers are abundant

The flowers are cream yellow

Plants of the new *Leucanthemum* can be compared to plants of 'Leumayel', U.S. Plant Pat. No. 19,242. In side-by-side comparisons conducted by the inventor in Enkhuizen, The Netherlands, the plants of the new *Leucanthemum* differed from the plants of the cultivar 'Leumayel' in the following characteristics:

TABLE 1

DIFFERENCES BETWEEN THE NEW VARIETY 'LEUZ0006' AND A MOST SIMILAR VARIETY

| | 'LEUZ0006' | 'Leumayel' |
|---|---|---|
| Flower size: | Small | Large |
| Plant height: | Shorter | Taller |
| Cold induction of flower: | Not needed | Advisable |

The plant:

Parentage:

*Female parent*.—'S4463-2', a genetic pool selection, not patented.

*Male parent*.—Not known.

Propagation:

*Type cutting*.—Terminal cuttings.

*Time to initiate roots*.—19 days at 20 degrees C.

*Time to produce a rooted cutting*.—3.5 weeks.

*Root description*.—Fine, fibrous and white in color.

Plant description:

*General appearance*.—Big plant with abundant flowers plant with dark leaves early to flower.

*Branching habit*.—Basal branching.

*Plant height*.—32 cm.

*Plant spread*.—18 cm.

*Lateral branch description*.—

*Length*.—

*Primary*.—24 cm.

*Secondary*.—12 cm.

*Diameter*.—

*Primary*.—0.4 cm.

*Secondary*.—0.3 cm.

*Texture*.—Smooth, glabrous.

*Internode length*.—2.5 cm.

*Color*.—RHS 138A.

*Foliage description*.—

*Arrangement*.—Alternate.

*Length, mature leaves*.—11 cm.

*Width, mature leaves*.—3.5 cm.

*Shape*.—Lanceolate.

*Apex*.—Rounded to broadly acute.

*Base*.—Attenuate.

*Aspect*.—Arcuate.

*Margin*.—Dentate.

*Pubescence*.—

*Upper surface*.—Lightly pubescent.

*Lower surface*.—Lightly pubescent.

*Color young foliage, upper surface*.—RHS 137A.

*Color young foliage, lower surface*.—RHS 137B.

*Fully expanded foliage, upper surface*.—RHS 137A.

*Fully expanded foliage, lower surface*.—RHS 138A.

*Petiole*.—Absent.

*Veins, venation type*.—Pinnate.

*Veins, color upper surface*.—RHS 143A.

*Veins, color lower surface*.—RHS 143D.

Inflorescence:

*Bud (described before color developed)*.—

*Bud shape*.—Spherical.

*Bud diameter*.—1.2 cm.

*Bud length*.—0.7 cm.

*Bud color*.—RHS 137B.

*Appearance*.—

*Form*.—Actinomorphic.

*Inflorescence position*.—Terminal.

*Disc and ray floret arrangement*.—Acropetally on a capitulum.

*Number of inflorescences per plant*.—45.

*Lasting quality per flower*.—10 days.

*Fragrance*.—None.

*Size*.—

*Diameter*.—

*First flowers*.—10 cm.

*Last flowers*.—6 cm.

*Height*.—1.5 cm.

*Diameter of disc*.—2 cm.

*Ray florets*.—

*Length*.—3.1 cm.

*Width*.—1.1 cm.

*Shape*.—Oblanceolate.

*Apex*.—Tridentate.

*Base*.—Cuneate.

*Margin*.—Entire.

*Texture (both upper and lower surfaces)*.—Smooth, glabrous.

*Number per inflorescence*.—About 45.

*Color, when opening*.—

*Upper surface*.—RHS 8A.

*Lower surface*.—RHS 8B.

*Color fully opened*.—

*Upper surface*.—RHS 10D.

*Lower surface*.—RHS 10D.

*Disc florets*.—

*Length*.—0.6 cm.

*Width*.—0.1 cm.

*Shape*.—Elliptic.

*Number per inflorescence*.—234.

*Color*.—

*Immature*.—

*Apex*.—RHS 7B.

*Margin*.—RHS 154B.

*Mature*.—

*Apex*.—RHS 13C.

*Margin*.—RHS 7B.

*Phyllaries*.—

*Length*.—1.1 cm.

*Width*.—0.3 cm.

*Shape*.—Elliptic.

*Apex*.—Obtuse.
*Margin*.—Entire.
*Number per inflorescence*.—40.
*Arrangement*.—Imbricate whorls.
*Texture* (*both upper and lower surfaces*).—Smooth and glabrous with light pubescence present.
*Color*.—
*Upper surface*.—RHS 137C.
*Lower surface*.—RHS 138B.
*Peduncle*.—
*Length*.—4 cm.
*Diameter*.—0.4 cm.
*Aspect*.—Upright.
*Texture*.—Light pubescence present.
*Color*.—RHS 138A.

Reproductive organs:
*Androecium*.—
*Presence*.—On disc florets only.
*Number* (*per flower*).—1.
*Filament length*.—0.2 cm.
*Filament color*.—RHS 5B.
*Anthers*.—
*Shape*.—Oblong.
*Length*.—0.1 cm.
*Color*.—RHS 8B.
*Pollen*.—
*Color*.—RHS 8A.
*Amount* (*generally*).—Moderate.
*Gynoecium*.—
*Presence*.—On disc and ray florets.
*Pistils*.—
*Number*.—1.
*Length*.—0.5 cm.
*Style*.—
*Length*.—0.4 cm.
*Color*.—RHS 154C.
*Stigma*.—
*Shape*.—Bi-lobed.
*Color*.—RHS 7B.
*Seeds*.—None observed.
*Disease resistance*.—No resistance or susceptibility observed.
*Temperature tolerance*.—Cold tolerance to −20 degrees C.; Heat tolerance to 35 degrees C.
*Drought tolerance*.—Not drought tolerant.

What is claimed is:

1. A new and distinct cultivar of *Leucanthemum* plant named 'LEUZ0006', as substantially illustrated and described herein.

* * * * *